United States Patent
Kulakofsky et al.

(10) Patent No.: US 9,295,726 B2
(45) Date of Patent: Mar. 29, 2016

(54) MULTI-POLYMER COMPOSITIONS FOR TRANSDERMAL DRUG DELIVERY

(71) Applicant: Noven Pharmaceuticals, Inc., Miami, FL (US)

(72) Inventors: Joshua Kulakofsky, Miami, FL (US); Puchun Liu, Miami, FL (US)

(73) Assignee: NOVEN PHARAMCEUTICALS, INC., Miami, FL (US)

( * ) Notice: Subject to any disclaimer, the term of this patent is extended or adjusted under 35 U.S.C. 154(b) by 0 days.

(21) Appl. No.: 14/141,923

(22) Filed: Dec. 27, 2013

(65) Prior Publication Data

US 2014/0186424 A1 Jul. 3, 2014

Related U.S. Application Data

(60) Provisional application No. 61/747,117, filed on Dec. 28, 2012.

(51) Int. Cl.
*A61K 9/70* (2006.01)
*A61K 31/415* (2006.01)
*A61K 47/32* (2006.01)
*A61K 31/4168* (2006.01)

(52) U.S. Cl.
CPC .............. *A61K 47/32* (2013.01); *A61K 9/7053* (2013.01); *A61K 9/7061* (2013.01); *A61K 31/4168* (2013.01)

(58) Field of Classification Search
CPC ... A61K 9/7061; A61K 9/7053; A61K 47/32; A61K 31/4168

USPC ........................... 424/443; 427/2.31; 514/398
See application file for complete search history.

(56) References Cited

U.S. PATENT DOCUMENTS

| | | |
|---|---|---|
| 5,234,957 A | 8/1993 | Mantelle |
| 5,332,576 A | 7/1994 | Mantelle et al. |
| 5,446,070 A | 8/1995 | Mantelle |
| 5,719,197 A | 2/1998 | Kanios et al. |
| 5,958,446 A | 9/1999 | Miranda et al. |
| 6,024,974 A | 2/2000 | Li |
| 6,024,976 A | 2/2000 | Miranda |
| 6,210,705 B1 | 4/2001 | Mantelle et al. |
| 6,235,306 B1 | 5/2001 | Miranda et al. |
| 6,316,022 B1 | 11/2001 | Mantelle et al. |
| 6,348,211 B1 | 2/2002 | Mantelle et al. |

(Continued)

OTHER PUBLICATIONS

Prof. Dr. Thomas Nugent, Amine Based Pharmaceutical Drugs, Jacobs University [Downloaded from internet <URL: https://www.jacobs-university.de/ses/tnugent/research/chiralamines/drugs >] [Retrieved Apr. 1, 2015]), excerpt in action.*

(Continued)

*Primary Examiner* — Brian-Yong Kwon
*Assistant Examiner* — Miriam A Levin
(74) *Attorney, Agent, or Firm* — Foley & Lardner LLP

(57) ABSTRACT

Multi-polymer compositions for the transdermal delivery of drugs, such as amine-functional drugs, in a flexible, finite form are described. The compositions comprise a polymer matrix that includes a drug or a pharmaceutically acceptable salt thereof and a polymer matrix comprising acrylic polymer(s), polyisobutylene polymer(s) and styrene-isoprene-styrene block copolymer(s). Methods of manufacturing and methods of using the compositions also are described.

12 Claims, 2 Drawing Sheets

(56) References Cited

U.S. PATENT DOCUMENTS

| | | |
|---|---|---|
| 7,846,916 B2 | 12/2010 | Houze |
| 7,867,986 B2 | 1/2011 | Houze |
| 7,879,831 B2 | 2/2011 | Houze |
| 7,989,496 B2 | 8/2011 | Hartwig et al. |
| 7,993,671 B2 | 8/2011 | Mantelle et al. |
| 8,153,151 B2 | 4/2012 | Houze |
| 8,187,628 B2 | 5/2012 | Houze |
| 8,216,606 B2 | 7/2012 | Houze |
| 8,231,906 B2 | 7/2012 | Mantelle |
| 8,246,976 B2 | 8/2012 | Nguyen |
| 8,277,838 B2 | 10/2012 | Nguyen |
| 8,337,884 B2 | 12/2012 | Mantelle et al. |
| 8,343,538 B2 | 1/2013 | Kanios et al. |
| 8,632,802 B2 | 1/2014 | Kanios |
| 8,703,175 B2 | 4/2014 | Kanios et al. |
| 8,715,723 B2 | 5/2014 | Kanios et al. |
| 8,784,874 B2 | 7/2014 | Strauss |
| 8,784,877 B2 | 7/2014 | Houze et al. |
| 2006/0078601 A1* | 4/2006 | Kanios et al. ............... 424/449 |
| 2011/0129535 A1 | 6/2011 | Mantelle |
| 2011/0160245 A1 | 6/2011 | Mantelle et al. |
| 2011/0288124 A1 | 11/2011 | Mantelle et al. |
| 2013/0156815 A1 | 6/2013 | Mantelle |
| 2013/0317461 A1 | 11/2013 | Kanios et al. |
| 2013/0324575 A1 | 12/2013 | Mantelle et al. |
| 2014/0105979 A1 | 4/2014 | Liao et al. |
| 2014/0121611 A1 | 5/2014 | Lambert et al. |
| 2014/0179739 A1 | 6/2014 | Mantelle et al. |
| 2014/0182597 A1 | 7/2014 | Patel et al. |
| 2014/0188056 A1 | 7/2014 | Mori et al. |
| 2014/0200530 A1 | 7/2014 | Mantelle |

OTHER PUBLICATIONS

Sigma-Aldrich, Acrylate Polymers [Retrieved from internet <URL: http://www.sigmaaldrich.com/materials-science/material-science-products.html?TablePage=20202574>] [Downloaded Apr. 1, 2015]), excerpt in action.*

Henkel, Duro-Tak and Gelva transdermal Pressure Sensitive Adhesives, Product Selection Guide (Sep. 2013), [Retrieved from internet <URL: http://www.henkelna.com/us/content_data/330922_11061_LT5343_Product_selector2_Web863600.pdf>], 2 pages.*

U.S. Appl. No. 14/191,900, filed Feb. 27, 2014, Kanios.
U.S. Appl. No. 14/245,398, filed Apr. 4, 2014, Kanios.
U.S. Appl. No. 14/133,900, filed Dec. 19, 2013, Kanios.
U.S. Appl. No. 13/616,919, filed Sep. 14, 2012, Houze et al.
U.S. Appl. No. 14/208,398, filed Mar. 13, 2014, Liao et al.
U.S. Appl. No. 14/208,367, filed Mar. 13, 2014, Nguyen et al.
U.S. Appl. No. 14/208,380, filed Mar. 13, 2014, Nguyen et al.
U.S. Appl. No. 14/206,369, filed Mar. 12, 2014, Lambert et al.
U.S. Appl. No. 14/206,298, filed Mar. 12, 2014, Liao et al.
U.S. Appl. No. 14/208,348, filed Mar. 13, 2014, Liao et al.
International Search Report issued on Apr. 14, 2014 in application No. PCT/US2013/077934.

* cited by examiner

MULTI-POLYMER COMPOSITIONS FOR TRANSDERMAL DRUG DELIVERY

CROSS-REFERENCE TO RELATED APPLICATIONS

This application claims the benefit under 35 USC §119(e) to U.S. provisional application 61/747,117, filed Dec. 28, 2012, the entire contents of which are incorporated herein by reference in their entirety.

FIELD

Described here are multi-polymer compositions for transdermal drug delivery, methods of making them, and methods of effecting transdermal drug delivery using them. In some embodiments, the drug is an amine-functional drug, such as clonidine.

BACKGROUND

Many factors influence the design and performance of transdermal drug delivery compositions. These include the individual drugs themselves, the physical and chemical characteristics of the compositions' components and their performance and behavior relative to other components, external and environmental conditions during manufacturing and storage, properties of the application site, the desired rate of drug delivery and therapeutic onset, the desired drug delivery profile, and the intended duration of delivery, among others.

Compositions for the transdermal delivery of amine-functional drugs are known, but there remains a need for compositions that exhibit suitable physical and pharmacokinetic properties. Further, there remains a need for compositions that can provide drug delivery over a period of time of about 24 hours, or that can provide drug delivery over an extended period of time, such as a period of about 7 days.

SUMMARY

In accordance with some embodiments, there are provided multi-polymer compositions for the transdermal delivery of an amine-functional drug in the form of a flexible finite system for topical application, comprising a polymer matrix comprising (i) a therapeutically effective amount of an amine-functional drug; (ii) an acrylic polymer; (iii) a polyisobutylene polymer, and (iv) a styrene-isoprene-styrene block copolymer. In specific embodiments, the amine-functional drug comprises clonidine, and the polymer matrix may comprise about 1% to 10% clonidine.

In some embodiments, the polymer matrix comprises two or more acrylic polymers. In any embodiments, the polymer matrix may comprise a non acid-functional acrylic polymer. In any embodiments, the polymer matrix may comprise about 85% to 95% w/w acrylic polymer. In any embodiments, the polymer matrix may comprise about 3% to 5% w/w polyisobutylene polymer. In any embodiments, the polymer matrix may comprise about 1% to 2% w/w styrene-isoprene-styrene block copolymer.

In any embodiments, the polymer matrix may have a coat weight of about 10 to 15 mg/cm$^2$.

In some embodiments, the system achieves delivery of the amine-functional drug over a period of time of about 24 hours. In other embodiments, the system achieves delivery of the amine-functional drug over a period of time of about 7 days.

In any embodiments, the system further comprises a backing layer and/or a release liner.

Also provided are methods for the transdermal delivery of an amine-functional drug, comprising topically applying a composition as described herein to the skin or mucosa of a subject in need thereof.

Also provided are methods for the manufacture of a composition as described herein, comprising:
optionally, drying one or more of an acrylic polymer, a polyisobutylene polymer, and a styrene-isoprene-styrene block copolymer to remove any solvent;
dissolving an acrylic polymer, a polyisobutylene polymer, and a styrene-isoprene-styrene block copolymer in a solvent miscible with the amine-functional drug and polymer components and mixing to form a polymer blend;
adding the amine-functional drug to the polymer blend and mixing to form a polymer matrix;
applying the polymer matrix to a release liner;
removing solvent from the polymer matrix; and
providing the polymer matrix with a backing layer.

In specific embodiments, the amine-functional drug is clonidine and the solvent is toluene.

DETAILED DESCRIPTION

Figure 1:
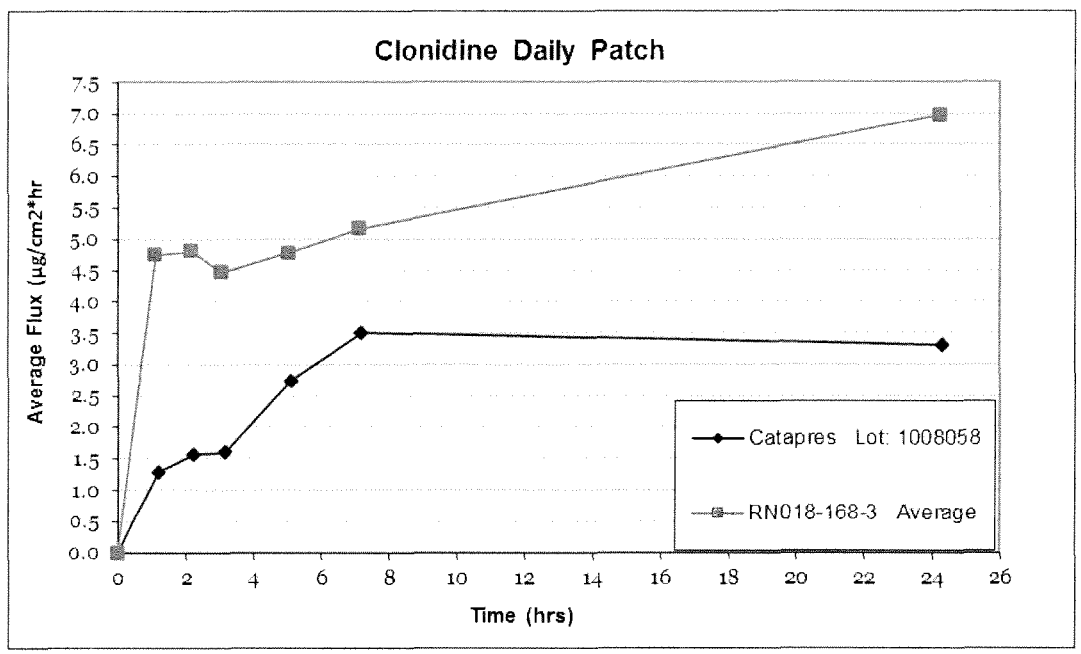
FIG. 1 shows the results of in vitro drug flux studies of clonidine from a 1 day multi-polymer system described herein (■) as compared to the commercially available Catapres-TTS® transdermal clonidine patch (♦).

Described herein are multi-polymer compositions, methods of making them, and methods for effecting the transdermal delivery of a drug, such as an amine-functional drug, using them. The compositions are provided in a flexible, finite form (e.g., "patch"-type systems) that comprise a polymer matrix that includes a drug or a pharmaceutically acceptable salt thereof, and that also is provided with a backing layer. The compositions exhibit satisfactory physical properties while also achieving satisfactory pharmacokinetic profiles. In specific embodiments, the polymer matrix comprises (i) a therapeutically effective amount of an amine-functional drug or pharmaceutically acceptable salt thereof; (ii) one or more acrylic polymer(s); (iii) one or more polyisobutylene polymers, and (iv) one or more styrene-isoprene-styrene block copolymers. In accordance with any embodiments, the polymer matrix may further comprise one or more penetration enhancers, and other excipients conventionally used in polymer matrix-type transdermal drug delivery compositions.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described.

Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free of" as used herein means that the described composition (e.g., polymer matrix, etc.) comprises less than about 5%, less than about 3%, or less than about 1% by weight, based on the total weight of the composition at issue, of the excluded component(s). The phrase "free of" as used herein means that the described composition (e.g., polymer matrix, etc.) is formulated without adding the excluded component(s) as an intended component, although trace amounts may be present in other components or as a by-product or contaminant, such that the composition comprises at most only trace amounts of the excluded component(s).

As used herein "subject" denotes any mammal in need of drug therapy, including humans. For example, a subject may be suffering from or at risk of developing a condition that can be treated or prevented with an amine-functional drug, or may be taking an amine-functional drug for other purposes.

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, the compositions described herein may be applied topically to a subject to achieve transdermal delivery of an amine-functional drug.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

The compositions described herein are in a "flexible, finite form." As used herein, the phrase "flexible, finite form" means a substantially solid form capable of conforming to a surface with which it comes into contact, and capable of maintaining contact so as to facilitate topical application. Such systems in general are known in the art and commercially available, such as transdermal drug delivery patches.

The compositions comprise a drug-containing polymer matrix that releases the drug upon application to the skin (or any other surface noted above). The compositions in flexible, finite form also include a backing layer in addition to the drug-containing polymer matrix layer. In some embodiments, the compositions in flexible, finite form may include a release liner layer in addition to a drug-containing polymer matrix layer and backing layer.

As used herein, "drug-containing polymer matrix" refers to a polymer composition which contains one or more drugs or pharmaceutically acceptable salt thereof and a polymer, such as a pressure-sensitive adhesive polymer or a bioadhesive polymer. A polymer is an "adhesive" or "bioadhesive" if it has the properties of adhesiveness per se. Other polymers can function as an adhesive or bioadhesive by the addition of tackifiers, plasticizers, crosslinking agents or other excipients. Thus, in some embodiments, the polymer optionally comprises tackifiers, plasticizers, crosslinking agents or other additives known in the art.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers or other additives. The term pressure-sensitive adhesive also includes mixtures of different polymers.

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

In some embodiments, the compositions in flexible, finite form are "monolithic" or "monolayer" systems, such that the drug-containing polymer matrix layer is the only polymeric layer present other than the backing layer and the release liner, if present. In such embodiments, the polymer matrix functions as both the drug carrier and the means of affixing the system to the skin or mucosa.

Polymer Matrix

In accordance with some embodiments, the compositions described herein comprise a polymer matrix that comprises, consists essentially of, or consists of, one or more drugs and/or pharmaceutically acceptable salt(s) thereof and acrylic polymer(s), polyisobutylene polymer(s), and styrene-isoprene-styrene block copolymer(s). In this context, the phrase "consists essentially of" means that the polymer matrix is substantially free of other polymer components (e.g., substantially free of polymers other than acrylic polymer(s), polyisobutylene polymer(s), and styrene-isoprene-styrene block copolymer(s)) and skin penetration enhancers, although it may include other excipients known to be useful in transdermal compositions (such as tackifiers, plasticizers, crosslinking agents or other excipients known in the art) as long as those other excipients do not degrade the physical and/or pharmacokinetic properties of the compositions to pharmaceutically unacceptable levels. In accordance with some embodiments, the compositions described herein comprise a polymer matrix that comprises, consists essentially of, or consists of, one or more drugs and/or pharmaceutically acceptable salt(s) thereof and acrylic polymer(s), polyisobutylene polymer(s), and styrene-isoprene-styrene block copolymer(s), and, optionally, one or more skin penetration enhancers. In some embodiments, the compositions described herein are free of or are substantially free of silicone polymer(s).

Amine-Functional Drugs

Although the compositions described herein may be useful for any drug(s), in accordance with some embodiments the compositions comprise one or more amine-functional drugs. The term "amine-functional" denotes a drug or active agent that contains one or more primary amine radicals such as phenylpropanolamine, secondary amine radicals such as propranolol, tertiary amine radicals such as theophylline and chlorpheniramine. The term "amine-functional" also includes heterocyclic amine radicals such as those found in theophylline and diethylcarbomazine and salts of amine-functional drugs such as scopolamine hydrobromide provided that they can be delivered transdermally, but does not include oxidized nitrogen radicals such as nitro radicals. Other examples of amine-functional drugs for transdermal drug delivery include, for example, tetracain, ephedrine, clonidine, nicotine, ramipril, enalapril, fentanyl and analogs such as alfentanyl, carfentanyl, lofentanyl, remifentanyl, sufentanyl, and trefentanyl, amphetamine, dextroamphetamine, methamphetamine, and atropine. Further examples of amine-functional drugs for use in transdermal drug delivery systems will be apparent to those skilled in the art. In specific embodiments, the compositions comprise clonidine. In further specific embodiments, the compositions comprise clonidine as the only drug component.

Drug concentration for use according to the present invention is drug dependent, but typically is below about 20% by dry weight of the composition, and often is below 10%.

The compositions described herein may be formulated with a drug in its free base form, or as any pharmaceutically acceptable salt or ester thereof, or any combinations thereof. Exemplary suitable pharmaceutically acceptable salts are salts of weak inorganic and organic acids, and quaternary ammonium salts. These include without limitation, salts with acids such as sulfuric, phosphoric, hydrochloric, hydrobromic, hydriodic, sulfamic, citric, lactic, maleic, malic, succinic, tartaric, cinnamic, acetic, benzoic, gluconic, or ascorbic acid, or quaternary ammonium salts with organic esters of sulfuric, hydrohalic, or aromatic sulfonic acids, such as methyl chloride, methyl bromide, ethyl chloride, propyl chloride, butyl chloride, isobutyl chloride, benzylchloride, benzyl bromide, phenethyl bromide, naphthymethyl chloride, dimethyl sulfate, methyl benzenesulfonate, ethyl toluenesulfonate, ethylene chlorohydrin, propylene chlorobydrin, allyl bromide, methylallyl bromide or crotyl bromide esters.

The compositions described herein include a therapeutically effective amount of drug or pharmaceutically acceptable salt(s) thereof. Generally, the amount of drug is from about 0.1% to about 50%, including from about 1% to about 20%, such as from about 1% to about 10% by weight, such as about 1, about 2, about 3, about 4, about 5, about 6, about 7, about 8, about 9 or about 10% by weight, based on the total dry weight of the polymer matrix. In specific embodiments, the polymer matrix comprises about 3, about 4, about 5, about 6, or about 7% by weight clonidine, based on the total dry weight of the polymer matrix.

In accordance with any of the embodiments described herein, the composition may include at least an amount of drug (such as clondine) or an equivalent amount of a pharmaceutically acceptable salt thereof for a 1 day product, and at least a proportionate amount for a 7 day product. For example, clonidine currently is typically administered at doses of about 0.1, 0.2 or 0.3 mg/day in the Catapres-TTS® transdermal patch. (The Catapres-TTS® product is a multilayer product comprising an adhesive layer, a rate control membrane, and a drug reservoir layer, in addition to a backing layer and release liner. The drug reservoir layer is an adhesive formulation of clonidine, mineral oil, polyisobutylene and colloidal silicone dioxide.)

Acrylic Polymers

As noted above, in some embodiments the polymer matrix comprises one or more acrylic polymers, such as one or more pressure-sensitive adhesive acrylic polymers. Acrylic polymers suitable for use in polymer matrix compositions are known.

In accordance with specific embodiments, the polymer matrix comprises one or more non-acid functional acrylic polymers. Non acid-functional acrylic polymers include those formed from acrylic esters copolymerized with other monomers that do not include acid-functional groups. Non acid-functional acrylic polymers include homopolymers, copolymers, terpolymers, etc., of acrylic acids and esters. As used herein, "non-acid functional acrylic polymer" includes polymers that include monomers that have one or more amide groups.

Suitable acrylic polymers can be obtained commercially or by polymerizing or copolymerizing suitable monomers such as acrylic monomers and other polymerizable monomers. Acrylate monomers which can be used include acrylic acid, methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate. In specific embodiments, the non acid-functional acrylic polymer includes methacrylate monomers and 2-ethylhexyl acrylate monomers. In other specific embodiments the non acid-functional acrylic polymer includes methacrylate monomers, 2-ethylhexyl acrylate monomers, and amide-group containing monomers.

In some embodiments, the non-acid functional acrylic polymer component of the polymer matrix consists of a single non-acid functional acrylic polymer. In other embodiments, the non-acid functional acrylic polymer component of the polymer matrix comprises a blend of a first at non-acid -functional acrylic polymer and a second non-acid functional acrylic polymer, and optionally includes additional (e.g., a third or more) non-acid functional acrylic polymers.

When the acrylic polymer component includes more than one non acid-functional acrylic polymer, the polymers can be present in any ratio that results in a product with satisfactory physical and pharmacokinetic properties. For example, the acrylic polymer component can include from 0-100% of a first non acid-functional acrylic polymer and from 100-0% of a second non acid-functional acrylic polymer, based on the total dry weight of the acrylic component, including about 10 to about 90%, about 15 to about 85%, about 20 to about 80%, about 25 to about 75%, about 33 to about 66%, and about 50% of the first non acid-functional acrylic polymer, and the balance being the second (or third, etc.) non acid-functional acrylic polymer(s).

Suitable acrylic polymers which are commercially available include those sold by Henkel (Dusseldorf, Germany), under the Duro-Tak® brand such as Duro-Tak 87-900A, Duro-Tak 87-9088, Duro-Tak 87-4098, or Duro-Tak 87-9900, and those sold by Monsanto (St. Louis, Mo.) under Gelva® Multipolymer Solution brand, such as Gelva 3087 and Gelva-3235.

In some embodiments, the polymer matrix includes one or more acrylic polymers that includes functional groups.

Acrylic-based polymers having functional groups are copolymers or terpolymers which contain, in addition to the non-functional monomer units described above, further monomer units having free functional groups. The monomers can be monofunctional or polyfunctional. These functional groups include carboxyl groups, hydroxy groups, amino groups, amido groups, epoxy groups, etc. Functional monomers that are copolymerizable alkyl acrylates or methacrylates include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate and other monomers having at least one unsaturated double bond which participates in copolymerization reaction in one molecule and a functional group on its side chain such as a carboxyl group, a hydroxyl group, a sulfoxyl group, an amino group, an amino group and an alkoxyl, etc. Further examples include monomers with at least one of the following moieties: alkylene, hydroxy-substituted alkylene, carboxylic acid-substituted alkylene, vynylalkanoate, vinylpyrrolidone, vinylpyridine, vinylpirazine, vinylpyrrole, vinylimidazole, vinylcaprolactam, vinyloxazole, vyinlacate, vinylpropionate and vinylmorpholine. Exemplary carboxyl functional monomers include acrylic acid, methacrylic acid, itaconic acid, maleic acid, and crotonic acid. Exemplary hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. The functional monomers may be present in any amount, such as from about of 0.1 to 50% by weight, based on the dry weight of the polymer, including about of 0.1 to 20% by weight, 0.1 to 15% by weight, 0.1 to 12% by weight, 0.1 to 10% by weight, and 0.1 to 8% by weight, based on the dry weight of the polymer.

Thus, the polymer matrix may include one or more non-acid functional acrylic polymers and, optionally, one or more functional acrylic polymers. When the acrylic polymer component includes both functional and non-acid functional acrylic polymers, the polymers can be present in any ratio that results in a product with satisfactory physical and pharmacokinetic properties. For example, the acrylic polymer component can include from 0-100% of non-acid functional acrylic polymer(s) and from 100-0% of functional acrylic polymer(s), based on the total dry weight of the acrylic component, including about 10 to about 90%, about 15-about 85%, about 20 to about 80%, about 25 to about 75%, about 33 to about 66%, and about 50% of non acid-functional acrylic polymer(s), and the balance being the functional acrylic polymer(s).

Other suitable acrylic polymers in addition to those mentioned above are known in the art. See, e.g., the non acid-functional acrylic polymers described in Satas, "Acrylic Adhesives, HANDBOOK OF PRESSURE-SENSITIVE ADHESIVE TECHNOLOGY, 2nd ed. , pp. 396-456 (D. Satas, ed.), Van Nostrand Reinhold, N.Y. (1989); "Acrylic and Methacrylic Ester Polymers," POLYMER SCIENCE AND ENGINEERING, Vol. 1, 2nd ed., pp 234-268, John Wiley & Sons, (1984).

Polyisobutylene Polymers

As noted above, in some embodiments the polymer matrix comprises one or more polyisobutylene polymers. Polyisobutylene polymers suitable for use in polymer matrix compositions are known, and include those sold by BASF under the Oppanol® brand, such as Oppanol® B11. In some embodiments, the polymer matrix comprises two or more polyisobutylene polymers of different molecular weights. In accordance with these embodiments, the relative amounts of polyisobutylene polymers can be selected and tailored to produce a product with satisfactory physical and pharmacokinetic properties.

SIS Block Copolymers

As noted above, in some embodiments the polymer matrix comprises one or more styrene-isoprene-styrene block copolymers. Styrene-isoprene-styrene block copolymers for use in polymer matrix compositions are known, such as those sold by Kraton under the Kraton® brand, such as Kraton® D111 KT.

As noted above, in some embodiments, the polymer matrices of the compositions described herein consist essentially of the drug or pharmaceutically acceptable salt(s) thereof and one or more of the polymer(s) described above, although such compositions may include other non-polymer components that do not degrade the physical and/or pharmacokinetic properties of the compositions to pharmaceutically unacceptable levels, such as one or more penetration enhancers, as discussed in more detail below. Further, as noted above, in some embodiments, the polymer matrices are free of or substantially free of silicone polymers.

Penetration Enhancers

As noted above, in some embodiments, the polymer matrices of the compositions described herein further comprise one or more penetration enhancers. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer. In specific embodiments the enhancer(s) serve to both enhance penetration of the drug through the stratum corneum and retain the drug at a site local to administration.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyidecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate. In some embodiments, combinations of two or more enhancers are used.

Generally speaking, the polymer matrices may include drug in an amount from about 1% to about 50%, including from about 1% to about 10%, such as from about 1% to about 5%, including about 1%, about 2%, about 3%, about 4% about 5%, about 6%, about 7%, about 8%, about 9%, or about 10% by weight, based on the total dry weight of the polymer matrix.

Generally speaking, the acrylic polymer(s) may be present in a range from about 50% to about 95%, including from about 75% to about 95%, such as from about 85% to about 95%, including from about 87% to about 91%, including about 88%, about 89%, and about 90%, by weight, based on the total dry weight of the polymer matrix.

Generally speaking, the polyisobutylene polymer(s) may be present in a range from about 1% to about 10%, including from about 2% to about 7%, including from about 3% to about 5%, including about 2%, about 2.5%, about 3%, about 3.5%, about 4%, about 4.5%, about 5%, about 5.5%, about 6%, about 6.5%, and about 7%, by weight, based on the total dry weight of the polymer matrix.

Generally speaking, the styrene-isoprene-styrene block copolymer(s) may be present in a range from about 0.1% to about 10%, including from about 1% to about 5%, including from about 1% to about 2%, including about 1.5%, about 2%, about 2.5%, about 3%, about 3.5%, about 4%, about 4.5%, and about 5%, by weight, based on the total dry weight of the polymer matrix.

Generally speaking, the penetration enhancer(s), if present, may be present in an amount from about 0.1% to about 10%, such as from about 0.1% to about 5%, including about 0.2%, about 0.4%, about 0.6%, about 0.8%, about 1.0%, about 2%, about 3%, about 4%, about 5%, about 6%, about 7%, about 8%, about 9%, or about 10%, by weight, based on the total dry weight of the polymer matrix. In embodiments using more than one enhancer, each may be present in any amount described herein (e.g., from about 0.1% to about 10%) or the total amount of enhancers may be within the amounts described herein (about 0.1% to about 10%).

While not wanting to be bound by any theory it is believed that the polymer blends described herein balance competing goals and properties of drug solubility, drug delivery and physical properties, such as wear properties. For example, while the acrylic polymers exhibit good solubility for amine-functional drugs, they generally have poor long-term wear properties. While silicone polymers have been used to improve the wear properties of acrylic-containing polymer matrices, silicone may interact with amine-functional drugs, leading to high peel force problems. The present inventors surprisingly found that multi-polymer matrix compositions comprising acrylic polymer(s), polyisobutylene polymer(s) and styrene-isoprene-styrene block copolymer(s) achieve desired drug delivery of amine-functional drugs while also exhibiting satisfactory storage and wear properties, and without suffering from high peel force problems. Thus, while not wanting to be bound by any theory, the present inventors believe that the polyisobutylene polymer(s) and styrene-isoprene-styrene block copolymer(s) improve the physical properties of the polymer matrix and improve the stability of the matrix composition both during the manufacturing process, and during storage and use.

Additionally, the multi-polymer matrix compositions described herein achieve desired drug delivery of amine-functional drugs, including relatively high drug flux and sustained drug delivery (including delivery over a period of 7 days), with relatively low drug loading.

Further, the use of two or more acrylic polymers in accordance with some embodiments described herein permits even greater control over the properties of the polymer matrix and the resulting pharmacokinetics of drug delivery. For example, two or more acrylic polymers may be selected with different solubilities for the specific drug(s) being formulated and/or with different physical properties (e.g., tack and wear).

Overall, the compositions described herein achieve effective, sustained drug delivery with relatively low drug loading, and exhibit good physical properties, including storage stability and wear properties.

Backing Layer

The compositions in flexible, finite form comprise a polymer matrix, such as described above, and a backing layer. The backing layer is impermeable to the drug (e.g., impermeable to the amphetamine) and is adjacent one face of the polymer matrix. The backing layer protects the polymer matrix from the environment and prevents loss of the drug and/or release of other components to the environment during use. The backing layer may be any backing layer known in the art for transdermal drug delivery systems.

Release Linter

The compositions in flexible, finite form may further comprise a release liner, typically located adjacent the opposite face of the system as compared to the backing layer. When present, the release liner is removed from the system prior to use to expose the polymer matrix layer prior to topical application. Materials suitable for use as release liners are well-known known in the art and commercially available, such as polyester release liners, including coated polyester release liners.

Methods of Manufacture

The compositions described herein can be prepared by methods known in the art. As one step, the polymer matrices described herein can be prepared by methods known in the art, such as blending (mixing) the polymer components in powder or liquid form with an appropriate amount of drug in the presence of an appropriate solvent, such as a volatile organic solvent, optionally with other excipients. To form a final product, the drug/polymer/solvent mixture may be cast onto a release liner (optionally, at ambient temperature and pressure) followed by evaporation of the volatile solvent(s), for example, at room temperature, slightly elevated temperature, or by a heating/drying step, to form the drug-containing polymer matrix on a release liner. A backing layer may be applied to form a final product.

An exemplary general method for preparing a unit final product of a composition as described herein in a flexible, finite form, is as follows:

1. Appropriate amounts of one or more polymers, solvent(s) and/or co-solvent(s), and optional excipient(s) are combined and thoroughly mixed together in a vessel.
2. The drug is added to the mixture and agitation is carried out until the drug is uniformly mixed therein.
3. The composition is transferred to a coating operation where it is coated onto a release liner at a controlled specified thickness. Solvent is removed from the coated composition, such as by passing the composition through an oven in order to drive off all volatile processing solvents.
4. The composition is provided with a backing layer, and optionally wound into rolls for storage until final processing.
5. Appropriate size and shape delivery systems are prepared, such as by die-cutting from the roll material, and then packaged into pouches.

The order of steps, the amount of the ingredients, and the amount and time of agitation or mixing may be important process variables which will depend on the specific polymers, active agents, solvents and/or cosolvents, and optional excipients used in the composition, but these factors can be adjusted by those skilled in the art. The order in which each method step is performed can be changed if needed without detracting from the invention.

The polymer matrix composition may be applied at a coat weight typical of those used in the art. In some embodiments, the polymer matrix composition is applied at a coat weight of about 10 mg/cm$^2$. In some embodiments, the polymer matrix composition is applied at a coat weight of about 12.5 mg/cm$^2$. In some embodiments, the polymer matrix composition is applied at a coat weight of about 15 mg/cm$^2$.

Polymer matrix compositions comprising acrylic polymer(s), polyisobutylene polymer(s) and styrene-isoprene-styrene block copolymer(s) also can be made by the following methods, which address the difficulties that can be encountered when blending acrylic polymer(s), and rubber polymers (such as polyisobutylene polymer(s) and styrene-isoprene-styrene block copolymer(s)) which generally do not blend well with each other. If any polymer component comprises any solvent, such as may result from the manufacturing process or as may be present in the polymer component as provided by the manufacturer/vendor, the solvent is removed. This can be done by any means known in the art, such as by drawing down a laminate of each polymer component on a release liner and drying the laminate, such as by exposing the laminate to elevated temperatures to evaporate any solvent present, such as by placing the laminate in an oven at an appropriate temperature and for an appropriate time. For the method, a solvent is selected that exhibits miscibility for the drug and polymer components, such as a solvent that will dissolve the drug and polymer components. For example, when the drug is clonidine, the solvent may be toluene. The polymer components are added to the solvent at an appropriate solids content for forming the matrix, e.g., to achieve a viscosity that is conducive to forming a stable blend. A typical solids content is between 30% and 50%. After the polymer components are blended, the drug is added and blended. Then, the manufacturing process can continue as outlined above, e.g., by coating the composition onto a release liner, providing a backing layer, and forming the final product.

In accordance with any of the embodiments of compositions described herein, the size of the final product is, in some embodiments, in the range of from about 2 cm$^2$ to about 100 cm$^2$, including 5 cm$^2$, 10 cm$^2$, 20 cm$^2$, 25 cm$^2$, 30 cm$^2$, 40 cm$^2$, 50 cm$^2$, 60 cm$^2$, 70 cm$^2$, 75 cm$^2$, 80 cm$^2$, and 90 cm$^2$.

Methods of Use

The compositions described herein are useful in methods for the transdermal delivery of any drug, and are particularly suited for amine-functional drugs. Thus, the compositions described herein can be used in the treatment of any condition that for which an amine-functional drug is prescribed. In the case of clonidine, for example, compositions described herein comprising clonidine are useful for the treatment of hypertension and other cardiovascular conditions. In such embodiments, a composition comprising a therapeutically effective amount of clonidine is topically applied to a subject in need thereof.

In some embodiments, the compositions achieve transdermal delivery of drug over a period of time of at least about 8 hours, including a period of time of at least about 8 hours to at least about 12 hours, at least about 24 hours, or longer. In other embodiments, the compositions achieve transdermal delivery of drug over a longer period of time, such as over a period of at least about 2 days, at least about 3 days, at least about 4 days, at least about 5 days, at least about 6 days, at least about 7 days, or longer.

The compositions described herein achieve a transdermal flux of drug (and/or one or more pharmaceutically acceptable salt(s) thereof) that is sufficient to have a therapeutic effect. As used herein, "flux" (also called "permeation rate") is defined as the absorption of a drug through skin or mucosal tissue, and is described by Fick's first law of diffusion:

$$J=-D(dCm/dx)$$

where J is the flux in g/cm$^2$/sec, D is the diffusion coefficient of the drug through the skin or mucosa in cm$^2$/sec and dCm/dx is the concentration gradient of the drug across the skin or mucosa.

In clonidine embodiments, the compositions described herein may achieve a transdermal flux of clonidine sufficient to deliver at least 0.1 mg, at least 0.2 mg, or at least 0.3 mg/day over the period of application, e.g., over a period of time of at about 24 hours (for a 1 day product) or over a period of time of about 7 days (for a 7 day product).

The following specific examples are included as illustrative of the compositions described herein. These example are in no way intended to limit the scope of the invention. Other aspects of the invention will be apparent to those skilled in the art to which the invention pertains.

Example 1

Multi-polymer matrix compositions as described herein are prepared as described above using toluene as the solvent during the manufacturing process.

TABLE 1

| | Comp. | | | | | | | | | |
|---|---|---|---|---|---|---|---|---|---|---|
| | 1 | 2 | 3 | 4 | 5 | 6 | 7 | 8 | 9 | 10 |
| | | | | | Sample | | | | | |
| | RN 018-168-3 | RN 018-169-2 | RN 018-180-1 | RN 018-180-2 | RN 018-180-3 | RN 018-180-5 | RN 018-180-6 | RN 018-181-2 | RN 018-181-4 | RN 018-181-6 |
| Clonidine | 6 | 4 | 3 | 5 | 7 | 4 | 6 | 5 | 4 | 4 |
| DT 87-900A | 25 | — | — | — | — | — | — | — | — | — |
| DT 87-9088 | 65 | 30 | 30 | 30 | 29 | — | — | 30 | — | 20 |
| DT 87-4098 | — | — | — | — | — | 30 | 29 | — | 30 | 50 |
| DT 87-9900 | — | 60 | 61 | 59 | 58 | 60 | 59 | 59 | 60 | 20 |
| Oppanol B11 | 3.0 | 4.5 | 4.5 | 4.5 | 4.5 | 4.5 | 4.5 | 4.5 | 4.5 | 4.5 |
| Kraton SIS | 1.0 | 1.5 | 1.5 | 1.5 | 1.5 | 1.5 | 1.5 | 1.5 | 1.5 | 1.5 |
| Coat Weight (mg/cm$^2$) | 10 | 10 | 10 | 10 | 10 | 10 | 10 | 15 | 15 | 10 |

DT 87-900 A=Duro-Tak® 87-900 A acrylic polymer
DT 87-9088=Duro-Tak® 87-9088 acrylic polymer
DT 87-4098=Duro-Tak® 4098 acrylic polymer
DT 87-9000=Duro-Tak® 87-9000 acrylic polymer
Oppanol B11=Oppanol® B11 polyisobutylene polymer
Kraton SIS=Kraton® SIS styrene-isoprene-styrene block copolymer Drug flux from Composition 1 over 24 hours was assessed and compared to drug flux from the commercial Catapres-TTS® 3 clonidine product (7.5 mg clonidine in a 10.5 cm² patch). Results are shown in FIG. 1. As the data demonstrate, Composition 1 achieved higher drug flux than the commercial product, even though it includes less drug per unit area (0.6 mg/cm² vs. 0.7 mg/cm²).

Figure 2:
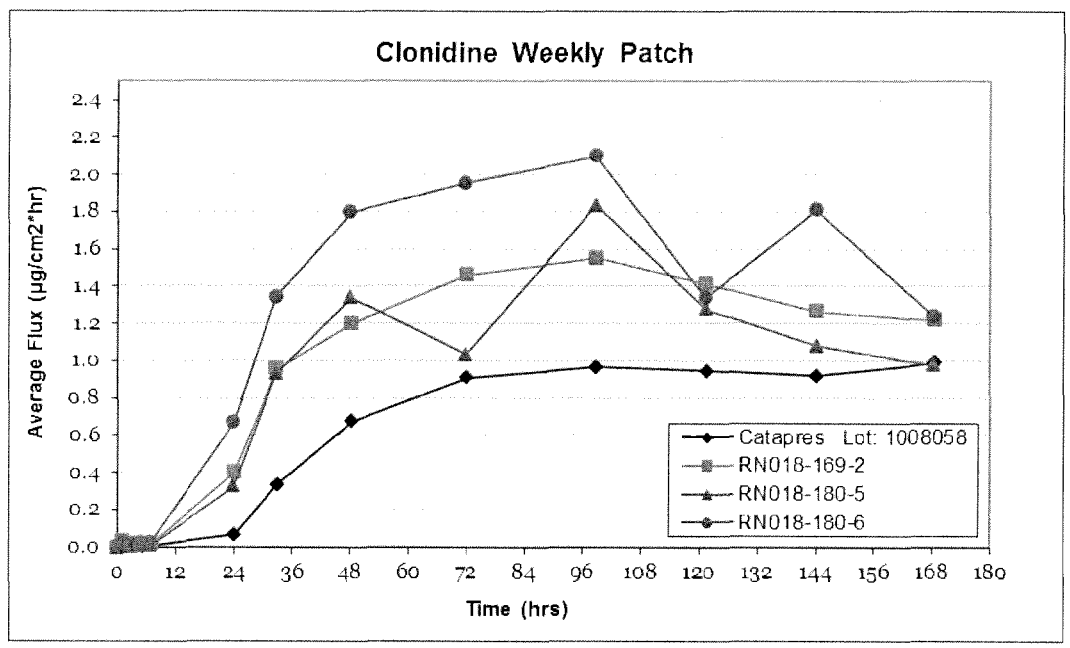
FIG. 2 shows the results of in vitro drug flux studies of clonidine from a 7 day multi-polymer system described herein (▲, ●, -x-) as compared to the commercially available Catapres-TTS® transdermal clonidine patch (♦).

Drug flux from Compositions 2, 6 and 7 over 7 days was assessed and compared to drug flux from the commercial Catapres-TTS® 3 clonidine product (7.5 mg clonidine in a 10.5 cm² patch). Results are shown in FIG. 2, where the top three line set forth data from Compositions 2, 6, and 7, and the bottom line sets forth data from Catapres-TTS® 3. As the data demonstrate, Compositions 2, 6 and 7, achieved higher drug flux than the commercial product, even though they include less drug per unit area (0.4 mg/cm² or 0.6 mg/cm² vs. 0.7 mg/cm²).

Example 2

Peel properties of the compositions of Example 1 were assessed by measuring the peel force needed to remove the polymer matrix from a stainless steel plate. The results are shown in Table 2.

TABLE 2

Peel from Stainless Steel Plate

| Lot # | High | Average | St. Dev (Avg.) |
|---|---|---|---|
| RN 018-180-1 | 171.2 | 144.0 | 23.0 |
| RN 018-180-2 | 170.3 | 212.0 | 6.38 |
| RN 018-180-3 | 252.4 |  | 22.7 |
| RN 018-180-5 | 334.2 | 311.9 | 12.3 |
| RN 018-180-6 | 334.7 | 296.2 | 5.15 |
| RN 018-181-2 | 339.5 | 286.0 | 8.96 |
| RN 018-181-4 | 378.8 | 343.8 | 14.2 |
| RN 018-181-6 | 300.6 | 279.4 | 9.07 |

The results show that the peel values vary with the composition, indicating that the different acrylic polymers and relative amounts thereof, as well as the amount of drug and coat weight, can impact peel values. The results therefore confirm that these properties can be selected and controlled to achieve desired physical properties.

What is claimed is:

1. A multi-polymer composition for the transdermal delivery of an amine-functional drug in the form of a flexible finite system for topical application, comprising a polymer matrix comprising (i) a therapeutically effective amount of an amine-functional drug; (ii) about 85% to 95% w/w of one or more non-acid functional acrylic polymers; (iii) about 3% to 5% w/w of a polyisobutylene polymer, and (iv) about 1% to 2% w/w of a styrene-isoprene-styrene block copolymer.

2. The composition of claim 1, wherein the amine-functional drug comprises clonidine.

3. The composition of claim 1, wherein the polymer matrix comprises two or more acrylic polymers.

4. The composition of claim 1, wherein the polymer matrix comprises about 1% to 10% w/w clonidine.

5. The composition of claim 1, wherein the polymer matrix has a coat weight of about 10 to 15 mg/cm².

6. The composition of claim 1, wherein the system achieves delivery of the amine-functional drug over a period of time of about 24 hours.

7. The composition of claim 1, wherein the system achieves delivery of the amine-functional drug over a period of time of about 7 days.

8. The composition of claim 1, further comprising a backing layer.

9. The composition of claim 1, further comprising a release liner.

10. A method for the transdermal delivery of an amine-functional drug, comprising topically applying a composition according to claim 1 to the skin or mucosa of a subject in need thereof.

11. A method for the manufacture of a composition as claimed in claim 9, comprising:
    optionally, drying one or more of the one or more non-acid functional acrylic polymers, the polyisobutylene polymer, and the styrene-isoprene-styrene block copolymer to remove any solvent;
    dissolving the one or more non-acid functional acrylic polymers, polyisobutylene polymer, and styrene-isoprene-styrene block copolymer in a solvent miscible with the amine-functional drug and polymer components and mixing to form a polymer blend;
    adding the amine-functional drug to the polymer blend and mixing to form a polymer matrix;
    applying the polymer matrix to a release liner;
    removing solvent from the polymer matrix to obtain a polymer matrix comprising (i) a therapeutically effective amount of the amine-functional drug; (ii) about 85% to 95% w/w of the one or more non-acid functional acrylic polymers; (iii) about 3% to 5% w/w of the polyisobutylene polymer and (iv) about 1% to 2% w/w of the styrene-isoprene-styrene block copolymer; and
    providing the polymer matrix with a backing layer.

12. The method of claim 11, wherein the amine-functional drug is clonidine and the solvent is toluene.

* * * * *